United States Patent [19]

Yukl

[11] 4,234,844

[45] Nov. 18, 1980

[54] ELECTROMAGNETIC NONCONTACTING MEASURING APPARATUS

[75] Inventor: Tex N. Yukl, Banks, Oreg.

[73] Assignee: Near Field Technology Co., Portland, Oreg.

[21] Appl. No.: 969,985

[22] Filed: Dec. 15, 1978

Related U.S. Application Data

[63] Continuation of Ser. No. 792,528, May 2, 1977, abandoned.

[51] Int. Cl.³ ............................................ G01R 27/04
[52] U.S. Cl. ............................................... 324/58.5 A
[58] Field of Search ..................... 324/58.5 A, 58.5 R, 324/58.5 B

[56] References Cited

U.S. PATENT DOCUMENTS 3,810,005  5/1974  Bennion et al. ............... 324/58.5 A

*Primary Examiner*—Stanley T. Krawczewicz
*Attorney, Agent, or Firm*—Kolisch, Hartwell & Dickinson

[57] ABSTRACT

A noncontacting apparatus and method for following the changes in impedance of a substance located within a specified investigation zone. A bidirectionally focused electromagnetic beam, having a pair of foci, is aimed with one of its foci located adjacent such a zone. A receiver located adjacent the other one of its foci is monitored for electrical changes therein, and such changes are interpreted as indications of impedance changes in the selected zone.

8 Claims, 4 Drawing Figures

ELECTROMAGNETIC NONCONTACTING MEASURING APPARATUS

CROSS-REFERENCE TO RELATED APPLICATION

This is a continuation of my prior-filed copending application entitled "Electromagnetic Noncontacting Measuring Apparatus", Ser. No. 792,528, filed May 2, 1977, now abandoned.

BACKGROUND AND SUMMARY OF THE INVENTION

It is well recognized that various conditions within various substances have or produce electrical effects which, if monitorable, can give an indication of the nature of such an internal condition. For example, it is known that conditions within various parts of the human body have electrical characteristics, such as differing impedances, which directly reflect such conditions. Further, conditions such as cracks and/or other flaws in various materials have or produce directly related electrical characteristics.

It is desirable to be able, in many instances, to follow, detect or monitor such conditions in a nonevasive, noncontacting, nondamaging manner.

While it is recognized that there are many applications for the apparatus and method of the invention, a preferred embodiment and method are described herein in connection with monitoringconditions within a portion of a human body, such as within a person's heart. This is a field in which the invention has been found to have particular utility.

The present invention recognizes and takes advantage of a well-known standing-wave phenomenon present with electromagnetic radiation wherein, at predetermined regular wavelength-related intervals along a transmission medium, wherein such radiation is present, directly related electrical voltage and current conditions exist. This phenomenon, and the theory underlying the instant invention, are set forth in many texts, including *Electronic and Radio Engineering* (4th Ed. 1955), Secs. 4–11 (McGraw-Hill Electrical and Electronic Engineering Series); and W. Johnson, *Transmission Lines and Networks* (1950), (McGraw-Hill Electrical and Electronic Engineering Series). There is proposed for use in the present invention a bidirectional microwave antenna which is capable of bidirectionally radiating and focusing microwave energy at a pair of spaced focal points that are spaced apart by a distance substantially equaling one-half the wavelength of the radiated energy. The antenna features a central ring-like radiation-effective expanse which functions as the driven element in the antenna, and in conjunction with this expanse director rings and a focusing lens that produce simultaneously on opposite sides of the antenna the two focal points just mentioned.

Working in conjunction with this antenna is a tubular receiver which is located adjacent one of the focal points, and which has a size that defines, in essence, the overall resolution of the system. In other words, the size of the receiver defines the size of the region that may be investigated for electrical characteristics. Working in cooperation with these two elements are a conventional source of electromagnetic energy which feeds the same to the antenna for transmission, and a conventional demodulator circuit connected both to this source and to the receiver for monitoring the amplitude of a signal received by the receiver and for comparing this signal, in a phase sense, with that produced by the source.

In operation, the antenna is aimed so as to place the other one of its focal points, i.e. that which is spaced from the one near the receiver, closely adjacent the particular region within a body wherein electrical characteristics, such as impedance, are to be monitored. With the source operating, the voltage and current conditions which exist in this space within a body are determined by the instantaneous impedance of such space. These voltage and current conditions are instantaneously reflected, in an inverse fashion, by related voltage and current conditions at the receiver. In other words, respecting whatever occurs impedance-wise at the zone within the body which is being investigated, related electrical changes occur at the location of the receiver.

Through monitoring, or perhaps more accurately through demodulating, the received signal, to detect amplitude and to compare phase with that of the source, what occurs electrically at the receiver is directly interpretable as an indication of impedance, and/or instantaneous changes of impedance, in the investigated zone. Through such monitoring, and through an understanding of what physical conditions within the zone produce such impedance conditions, the desired physiologic or other conditions within the investigated zone are determinable.

The operation just described may be performed at a relatively low power level. Hence, the likelihood of radiation damage in the investigated zone is extremely low. Further, it is an extremely simple matter to locate the investigated zone wherever desired. This may be done simply by shifting the location and/or orientation of the antenna relative to the investigated body. Further, the resolution of the system is easily controlled through selection of the size of the receiver. More specifically, a larger zone, with lower resolution, may be achieved through using a larger receiver located a somewhat greater distance from its adjacent focal point of the antenna. Greater resolution, with investigation of a smaller zone, is achieved by going in the reverse direction, i.e. through using a smaller receiver located closer to its adjacent focal point. Obviously, the investigation performable by the apparatus of the invention does not require any physical invasion of the body wherein investigation is made.

These and other objects and advantages attained by the invention will become more fully apparent as the description which now follows is read in conjunction with the accompanying drawings.

DETAILED DESCRIPTION OF THE INVENTION

Figure 1:
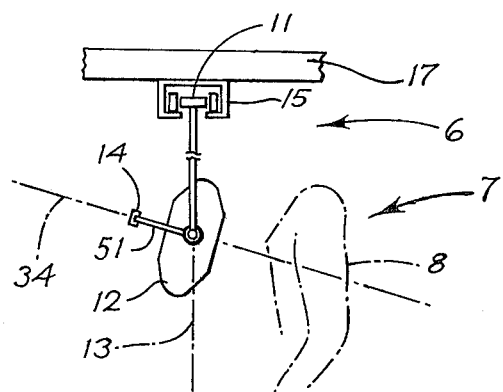
FIG. 1 is a simplified fragmentary side elevation showing a portion of a diagnostic system which employs the present invention.
Figure 2:
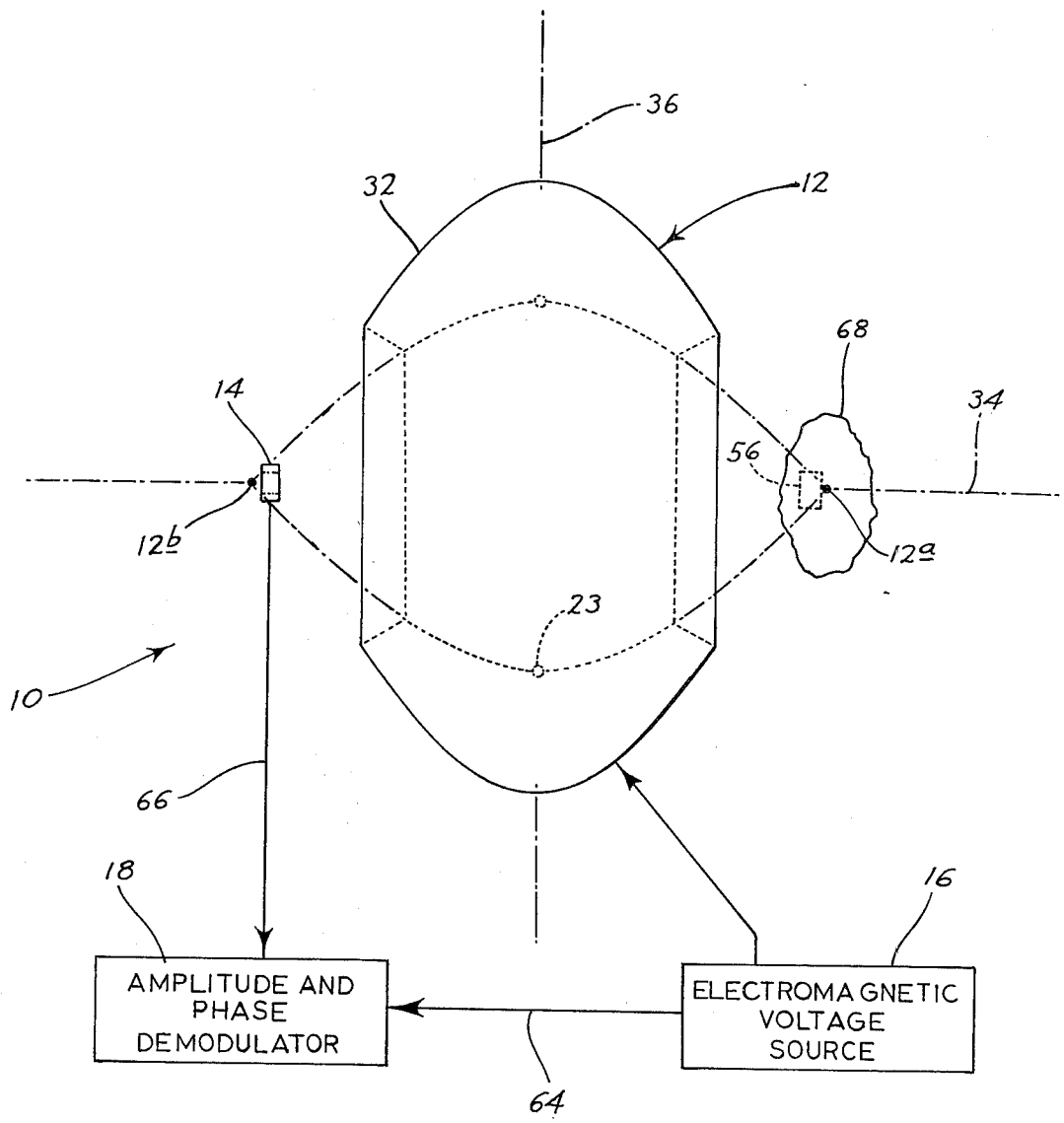
FIG. 2 shows schematically, on a somewhat larger scale, and in block form, the apparatus of the invention.

Turning now to the drawings, and referring first to FIGS. 1 and 2, indicated generally at 10 (see FIG. 2) is an apparatus for following, or monitoring, an electrical characteristic, such as electrical impedance, within a selected interrogation zone inside of a substance, such as the heart wall in a person's body. Apparatus 10 is used herein in a diagnostic system 6 (see FIG. 1) which includes a patient-positioning station 7 wherein a portion of a patient's body is shown in dashed outline at 8.

Included in system 10 are a special bidirectional focusing antenna 12 for electromagnetic radiation, a receiver 14 which works in conjunction with antenna 12, a source 16 of electromagnetic voltage, and an amplitude and phase demodulator 18. While different particular frequencies may be used, a frequency that has been selected for system 10 is about 505 megahertz, which constitutes what is commonly referred to as a microwave frequency. Radiation at this frequency has a wavelength of about 23.5-inches.

Antenna 12, the construction of which will be described shortly, is pivotally mounted on an overhead yoke 9 which attaches to the diametrally opposite sides of the antenna, and which mounts the same for pivoting about a substantially horizontal axis which is normal to the plane of FIG. 1. Yoke 9 is suspended from a carriage 11, and more particularly is journaled on the carriage for rotating about a substantially vertical axis shown at 13. Carriage 11 is roller-mounted on a track 15 for translational movement toward and away from the viewer in FIG. 1. Finally, track 15 is roller-mounted (in a conventional way) on another track 17 which is disposed normal to track 15, and which permits translational movement of the antenna from left to right in FIG. 1. In the particular diagnostic system illustrated herein, it is not necessary to provide for vertical translation of the antenna. However, were such required, it would be a simple matter to construct an extensible portion in yoke 9 that would be operable to permit this kind of movement.

Figure 3:
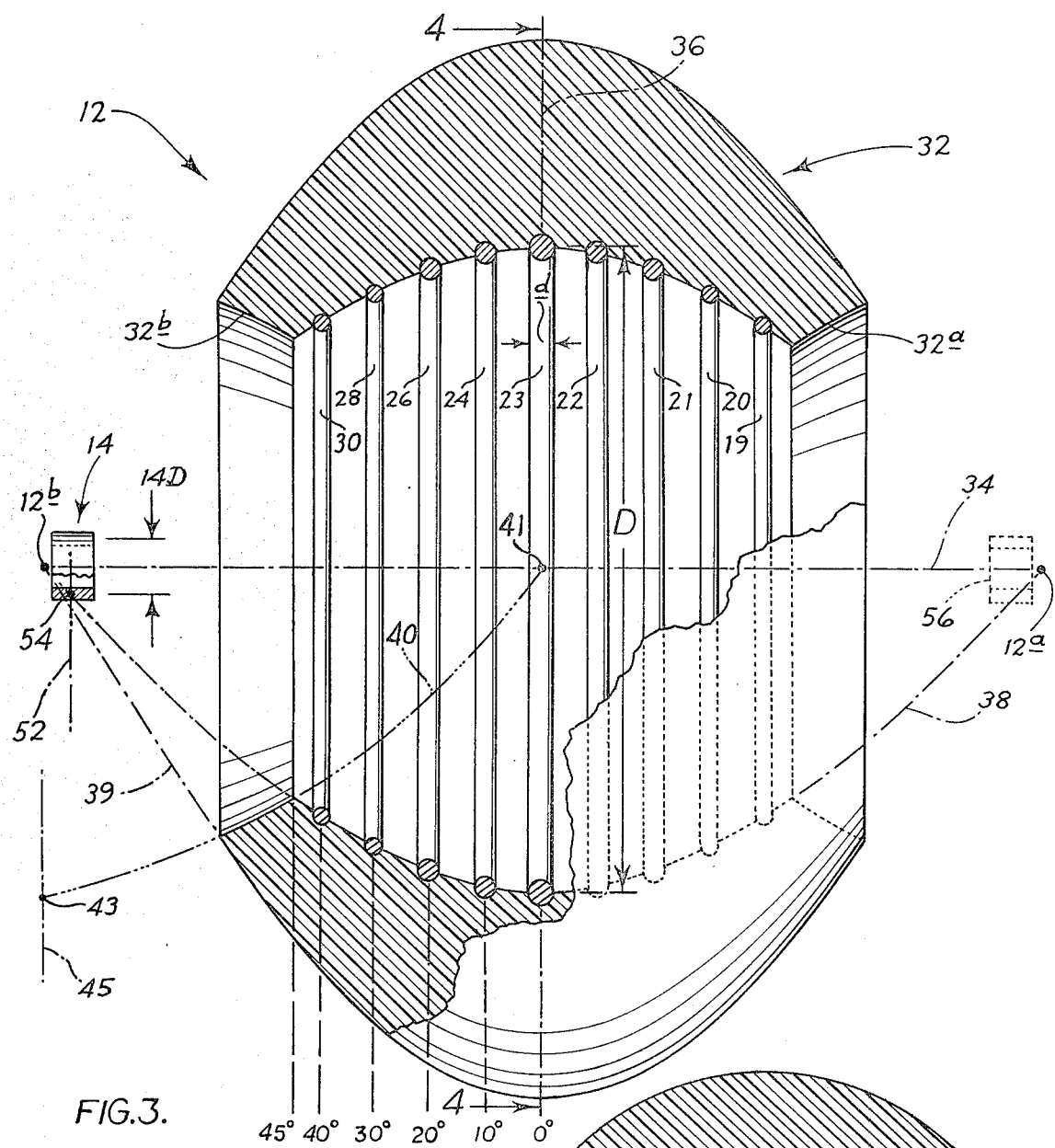
FIG. 3 is an enlarged side elevation, partly in cross-section, illustrating an antenna and a receiver which are used in the apparatus of the invention.
Figure 4:
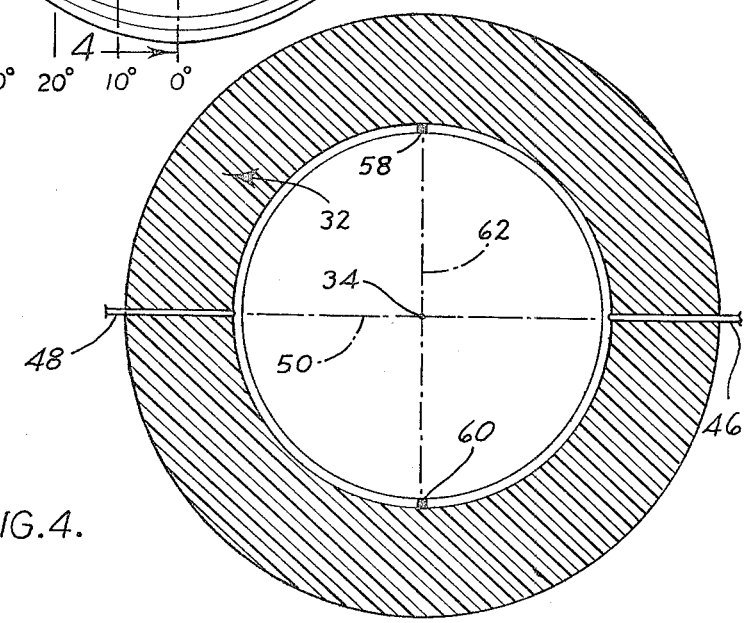
FIG. 4 is a cross-sectional view, on about the same scale as FIG. 2, taken generally along the line 4—4 in FIG. 3.

Describing now the construction of antenna 12, and referring to FIGS. 3 and 4, in general terms, the antenna comprises a plurality of conductive, continuous circular rings, shown at 19, 20, 21, 22, 23, 24, 26, 28, 30, which are mounted within a generally donut-shaped housing 32 that functions as a focusing lens in the antenna.

All of these rings are substantially planar, and continuous or unbroken. The rings are formed of a solid copper wire having a circular cross section. These rings are disposed with their planes substantially parallel to one another, and perpendicular to the transmission axis 34 of the antenna. The planes containing these rings are equally spaced, in a manner which will be described shortly. Ring 23 is the largest among the rings, and occupies what might be referred to as the central plane 36 of the antenna. It is referred to as the driven ring.

The other rings in the antenna are referred to as director rings. It is believed obvious from a study of FIG. 3 that, advancing in both directions away from plane 36, the director rings become progressively smaller. Thus, rings 22, 24 are somewhat smaller than ring 23, but are equal in size to each other. Rings 21, 26 are smaller than rings 22, 24, and also are of equal size. Likewise, rings 20, 28 and rings 19, 30 are progressively smaller, with rings 20, 28 being of equal size, and the same also being true of rings 19, 30.

Antenna 12 herein is constructed to work at the abovementioned frequency (505 megahertz). For a reason which will shortly be explained, it is desirable that the "nominal" circumference of driven ring 23 be substantially exactly equal to the wavelength of the selected frequency. Hence, the nominal circumference of ring 23, i.e. that circumference measured about a circular line within the body of the ring centrally between the inside and outside diameters of the ring, is about 23.5-inches.

With the nominal circumference of ring 23 thus defined, the "nominal" diameter of the ring, shown as dimension D in FIG. 3, is also determined. As was mentioned earlier, the cross-sectional area of the solid wire making up each ring is circular. Referring again specifically to ring 23, the diameter of this cross-sectional area is shown at d in FIG. 3. With the nominal diameter of the overall ring determined as just indicated, dimension d is determined in accordance with the following formula:

$$Z = 276 \, (\log(2D/d))$$

Where Z equals the characteristic impedance of the antenna, D is the nominal diameter of a ring, such as ring 23, and d is the diameter of the cross-sectional area of the ring material, such as dimension d in FIG. 3.

In order to obtain maximum effectiveness in apparatus 10, it is desirable that the characteristic impedance of the antenna be as closely matched as possible to that of the medium wherein monitoring is desired. For example, and in the case of the antenna's being used as a means for monitoring electrical characteristics inside a person's body, it is desirable that the characteristic impedance in the antenna be closely matched to the mean impedance expected to be encountered in such a space. Antenna 12 has been so constructed, and to this end, experiments have shown that the mean impedance of tissue in a human body is around 487-ohms. Accordingly, this figure has been chosen to define the characteristic impedance of antenna 12.

From the above formula, dimension d is immediately calculatable, and turns out to be about 0.25-inches.

Turning for a moment to the construction of lens 32, the purpose of this lens is to create a pair of spaced focal points for the antenna, distributed symmetrically with respect to ring 23, and located on transmission axis 34. More specifically, lens 32 functions to create focal points 12a, 12b on axis 34, which points are each spaced along the axis substantially exactly one-quarter of the wavelength of the frequency mentioned above from plane 36. A material for lens 32 which functions satisfactorily for this purpose is polystyrene, and such material is used in lens 32.

A first important consideration for lens 32 is that it have an inside surface of revolution which, where it intersects a radial plane containing axis 34, curves along a substantially sinusoidal path that has a peak at the location of the nominal circumference location of ring 23, and which intersects axis 34 at focal points 12a, 12b. Such a path illustrated in dash-double-dot lines at 38 in FIG. 3. It is obvious from this requirement that the inside wall of the lens is suitably grooved so as to receive ring 23 to the depth indicated in FIG. 3. Further, it is desirable that the path thus followed by the inside surface of lens 32 terminate at what might be thought of as the 45° points on opposite sides of plane 36. Such an angular measurement, of course, relates to the angular condition of the sinusoidal course followed by path 38 relative to plane 36. This situation is illustrated in FIG. 3 along the degree-graph-axis presented in the figure.

A further consideration of lens construction is that the radial thickness of the lens, i.e. the radial dimension of the lens, measured from its inside surface to its outside surface in different axially displaced planes which intersect axis 34 at a right angle, be a predetermined fixed percentage of the inside circumference of the lens in each such plane. More specifically, it will be noted that, at the location of ring 23 where the nominal circumference of this ring coincides with path 38, such circumference is equal to the wavelength of the frequency of the antenna. The radial dimension of lens 32 in this plane, measured outwardly from the nominal circumference of ring 23, is preferably about one-tenth of this nominal circumference. This same relationship remains, progressing in axially opposite directions away from plane 36. Consequently, the outside surface of lens 32, where it intersects a radial plane containing axis 34, also follows a sinusoidal path 39, different from the first-mentioned sinusoidal path, which has a peak where it intersects plane 36, and which extends through focal points 12a, 12b. This kind of construction assures maximum efficiency in the lens.

Still another consideration of lens construction is that, at axially opposite ends thereof, the lens includes what are referred to as exit faces 32a, 32b, which face toward focal points 12a, 12b, respectively. Each of these exit faces, where it intersects a radial plane containing axis 34, curves along yet another sinusoidal path, similar to the first-mentioned sinusoidal paths, such as the path shown in dash-triple-dot lines at 40 in FIG. 3 for face 32b. Path 40 intersects axis 34 at 41 in the plane of ring 23, and has a "peak" 43 relative axis 34 where it intersects a plane 45 which contains focal point 12b and which is normal to axis 34. The extremities of faces 32a, 32b are defined by the intersection of paths 38, 39, and paths like path 40.

In order to inhibit radiation leakage through the wall of the lens, the outside surface is preferably coated with a suitable thin conductive layer, such as a suitable silver layer.

Considering the director rings, four such rings are used on each side of ring 23. These are spaced from each other, and from ring 23, by what might be thought of as 10° distances along the sinusoidal path of the inside surface of lens 32. This situation is illustrated by the intersections depicted for the planes of ring 24, 26, 28, 30 and the graph-degree-axis shown in FIG. 3. Each of the director rings has its nominal circumference defined by the circular path of intersection of the plane of the ring and the surface of revolution defining the inside surface of the lens. Hence, for each such ring the "D" dimension thereof is thus defined. The diameter of the cross-sectional area of the ring material for each such ring is determined, then, in accordance with the above given formula, wherein the characteristic impedance remains the same as that described earlier. As a consequence of this situation, not only do the nominal circumferences of the director rings, progressing away from ring 23, become smaller, but also the diameters of the cross-sectional areas of the rings become smaller. By way of illustration, Table I below sets forth some actual dimensions which have been used satisfactorily for the rings in antenna 12.

TABLE I

| Ring(s) | D (inches) | d (inches) |
| --- | --- | --- |
| 23 | 7.44 | 0.255 |
| 22, 24 | 7.339 | 0.251 |
| 21, 26 | 6.995 | 0.239 |
| 20, 28 | 6.446 | 0.221 |
| 19, 30 | 5.702 | 0.195 |

When antenna 12 is operated, ring 23 therein is driven by source 16 which operates at the frequency mentioned above. In order for transmission to occur best, in accordance with the present invention, it is important that this ring be driven at precisely diametrically opposed points on the ring. Referring especially to FIG. 4, conductors 46, 48 are provided which extend coaxially in a plane 50 (which is at a right angle relative to the plane of the figure), normal to axis 34, and connect with such diametrically opposed points on ring 23. These conductors may take any suitable form, and may be mounted in the wall of lens 32 in any suitable manner. Where they extend through the lens wall, they coincide with the horizontal pivot axis provided by yoke 9. With such connections made, plane 50 is referred to as the high-impedance plane in the antenna.

Still a further consideration with respect to operating antenna 12, it is important that connections extending between conductors 46, 48 and source 16 be sized to assure that signals fed to the diametrically opposed points of connection between ring 23 and conductors 46, 48 be substantially exactly 180° out of phase. Such connections form no part of the present invention, but are mentioned herein because they are important to assuring maximum efficient operation from the antenna. Those skilled in the art are well aware of how to achieve such connections.

As was mentioned earlier, receiver 14, in essence, defines the interrogation zone for the antenna. The purpose of the receiver is to respond to, or pick up, radiation directed by the antenna toward focal point 12b. Preferably, and as is the case in the construction shown herein, receiver 14 is located somewhat toward antenna 12 from focal point 12b. The receiver takes the form of a short length of conductive tubing. More specifically, the tube forming receiver 14 has an axial dimension, measured along axis 34, of about one-half inch, and a nominal diameter, indicated at 14D, also of about one-half inch. The wall thickness of the tube forming the receiver is about one-eighth of an inch. Receiver 14 is mounted coaxial with the antenna, and in any suitable fashion (as by a mount 51—see FIG. 1) locking it into the position shown in FIGS. 1 and 3 relative to the antenna. Preferably, the receiver is located relative to focal point 12b in such a manner that what might be thought of as its central axial plane 52, which is normal to axis 34, intersects path 38 where the latter intersects the nominal diameter of the receiver. This point of mutual intersection is indicated at 54 in FIG. 3.

The interrogation zone defined for antenna 12 is indicated by dashed block 56 in FIG. 1. Zone 56 is generally cylindrical, has substantially the same outside dimensions as receiver 14, and is located in what might be thought of as a mirror-image position on the opposite side of the antenna from receiver 14—slightly inwardly from focal point 12a.

When antenna 12 is used, electromagnetic energy from source 16 is supplied to ring 23 as previously mentioned. With such energy supplied, radiation takes place in axially opposite directions relative to ring 23 from a pair of diametrically opposed points (indicated as darkened regions 58, 60 in FIG. 4) which are in quadrature with the points of connection between ring 23 and conductors 46, 48. These two points lie in a common plane 62 which contains axis 34 and which is normal to the plane of FIG. 4. Radiation from these two points is focused by lens 32 toward focal points 12a, 12b. The fact that radiation takes place from point locations facilitates high resolution for the lens. The director rings function along with the lens to guide radiation toward points 12a, 12b.

With the focal points of the antenna located at quarter-wavelength distances from the plane of ring 23, voltage and current conditions which exist in zone 56, as a result of the impedance of material within this zone, produce related voltage and current conditions at receiver 14. As mentioned earlier, the theory behind such performance is well known. How it is used in apparatus 10 will be discussed shortly.

Connections for picking up a signal form receiver 14 are similar in nature to the driving connections made with ring 23. More specifically, these connections are preferably made in high-impedance plane 50, and with attention paid to the relative lengths of such connections so as to assure that signals received by the receiver are transmitted to demodulator 18 with a 180° phase relationship.

Completing now a description of the invention, and referring to FIG. 2, as was mentioned earlier, demodulator 18 is of conventional construction. Its purpose is to follow the amplitude of a signal received by receiver 14, and also to compare the phase of this signal with that of source 16. Accordingly, a suitable connection exists between source 16 and circuit 18, as indicated by line 64. Also, input connections for the demodulator are made from receiver 14, such connections being represented by line 66.

While various available devices may be used, respectively, for source 16 and demodulator 18, two such devices which are commercially available have been successfully used in the practice of this invention. More specifically, as a voltage source, I have used a sine wave generator, made by Tektronix, Inc. of Beaverton, Oregon, designated as model #SG504. Signals from this generator are derived, through a conventional "T-connection" for both the antenna and the demodulator from what is called the "leveled voltage" output terminal in the generator.

For demodulator 18, I have used a Hewlett-Packard model 432A Radio Frequency Power Meter, which is fed signals via a Hewett-Packard model 478A Thermister Mount. The Thermister Mount is supplied signals through a conventional "T-connection" both from source 16 and from receiver 14. I have used conventional isolation techniques to prevent incoming source and receiver signals from interfering with one another.

As was mentioned earlier, system 10 is used in the application now being described to investigate conditions within a person's heart wall. A portion of such a wall is shown generally fragmentarily at 68 in FIG. 2.

When it is desired to monitor the condition of heart wall 68, the antenna is maneuvered to place zone 56 at a particular region of interest inside this wall. Such a situation is shown schematically in FIG. 2.

Source 16 is operated, and when operating, supplies energy to antenna 12—which energy is then radiated bidirectionally, as explained, toward focal points 12a, 12b. Under these circumstances, the impedance condition of the heart wall within zone 56 affects the voltage and current conditions existing at that point in the radiated energy (as explained by conventional theory). Further, these voltage and current conditions, occurring within zone 56, produce related voltage and current conditions received by receiver 14 (as also explained by conventional theory).

With operation of the system as just described, the amplitude of the signal existing at receiver 14, and the phase relationship thereof with respect to that of the source, are monitored, and are directly interpretable as an indication of impedance conditions within zone 56. These conditions, in turn, and through knowledge of the functioning of the monitored zone, can be interpreted to indicate different particular physical conditions.

It will be obvious that simply by shifting the location and orientation of the antenna with respect to the body wherein investigations are being made, it is an extremely simple matter to locate zone 56 wherever desired.

Where substances other than living tissue are to be investigated, such as in a metal-flaw detection system, where different characteristic impedances exist, the sizing of parts is adjusted accordingly as mentioned earlier. Also, and through experience and calibration, changes observed in electrical impedance within a zone like zone 56, are directly interpretable to indicate internal physical conditions.

It is obvious that there is thus proposed a unique apparatus and method for monitoring a defined location within a substance to determine different specific electrical characteristics of the substance. This is done through the unique technique of bidirectionally producing a beam of focused electromagnetic radiation which, in one direction is focused toward an investigation zone, and in the opposite direction is focused toward a receiver. The invention takes advantage of the fact that in such a system, and where each focal point is, say, a quarter-wavelength distance from the central radiating plane of the antenna, the impedance of the substance in the investigation zone affects voltage and current conditions not only in that zone but also in the corresponding zone occupied by the receiver of the system, such as receiver 14. Hence, conditions occurring in the receiver can be monitored and interpreted directly to indicate conditions in the monitored zone. Obviously, no physical invasion is required of the monitored zone. Further, relatively low power levels of radiation may be used. As an illustration, tissue monitoring can satisfactorily be performed with a power level of about one microwatt per square centimeter in the investigated zone. Thus, radiation power per se does not pose any significant hazard.

While a preferred embodiment, and a method of practicing the invention have been described, it is appreciated that the invention has a huge number of applications which extend significantly beyond the two types of applications specifically mentioned herein. For example, wherever it is known that a condition within a substance can produce identifiable electrical characteristics, such a substance may be irradiated in accordance with the invention to detect internal characteristics. Accordingly, variations and modifications in the invention are known to be produceable without departing from the spirit of the invention.

It is claimed and desired to secure by Letters Patent:

1. Noncontacting apparatus for following an electrical characteristic of a substance located at a selected interrogation site, said apparatus comprising
   a source for producing electromagnetic energy,
   bidirectional, focusing, energy-directing means coupled to said source for bidirectionally directing energy produced thereby toward a pair of spaced foci, one of which is positioned adjacent said interrogation site, and
   monitoring means including sensor means located adjacent the other one of said foci for monitoring changes in electrical conditions occurring adjacent said other one of said foci.

2. The apparatus of claim 1, wherein said energy-directing means is mounted for movement so as to enable shifting of the location of said interrogation site, and said sensor means is fixed in position relative to said directing means.

3. The apparatus of claim 1 which is constructed specifically to follow electrical impedance.

4. The apparatus of claim 1, wherein said sensor means comprises conductive means for receiving energy directed by said energy-directing means toward said other one of said foci.

5. Noncontacting apparatus for following the impedance of a substance located at a selected interrogation site, said apparatus comprising
   a source for producing electromagnetic energy having a predetermined wavelength,
   a bidirectional focusing antenna coupled to said source for directing energy produced thereby toward a pair of spaced foci located symmetrically with respect to, and toward opposite sides of, said antenna, said foci being spaced by a distance substantially equalling one-half of said predetermined wavelength, with one of the foci being located adjacent said interrogation site,
   receiving means positioned adjacent the location of the other one of said foci, adapted to receive energy directed theretoward by said antenna, and
   means operatively connected to said receiving means for observing electrical conditions therein resulting from its receipt of energy from said antenna.

6. The apparatus of claim 5, wherein said antenna is mounted for movement so as to enable shifting of the location of said interrogation site, and said receiving means is fixed in position relative to said antenna.

7. A noncontacting method of following an electrical characteristic of a substance located at a preselected interrogation site, said method comprising
   generating a bidirectionally focused beam of electromagnetic energy, with such beam having a pair of spaced foci wherein an electrical change occurring at one effects a related electrical change at the other,
   orienting such a beam so as to place one of its foci adjacent the location of said preselected interrogation site, and
   with the beam so oriented, monitoring electrical conditions adjacent the location of the other one of its foci.

8. The method of claim 7, wherein said generating of a beam comprises producing a pair of spaced, related radiating points for electromagnetic energy, and bidirectionally focusing radiation from such points toward said foci.

* * * * *